US005571783A

United States Patent [19]
Montagne et al.

[11] Patent Number: 5,571,783
[45] Date of Patent: Nov. 5, 1996

[54] COMPOSITION AND METHOD FOR TREATING PATIENTS WITH HEPATIC DISEASE

[75] Inventors: Dirk H. Montagne, Grosshochstetten, Switzerland; Ahmad R. Kamarei, Wilmette, Ill.; Guy Vaussard, Blonay, Switzerland; Eric Leopold, Sunnyvale, Calif.; Susan Trimbo, Evanston, Ill.

[73] Assignee: Clintec Nutrition Company, Deerfield, Ill.

[21] Appl. No.: 28,373

[22] Filed: Mar. 9, 1993

[51] Int. Cl.$^6$ .................................................. A61K 31/195
[52] U.S. Cl. ........................ 514/2; 514/552; 514/893; 514/23; 426/656; 426/658; 424/195.1
[58] Field of Search ................................. 514/2, 23, 893, 514/552; 424/195.1; 426/656, 658

[56] References Cited

U.S. PATENT DOCUMENTS

| | | |
|---|---|---|
| Re. 30,753 | 9/1981 | Narasimhan et al. ............ 435/68 |
| 3,697,287 | 10/1972 | Winitz ........................ 99/14 |
| 3,698,912 | 10/1972 | Winitz ........................ 99/1 |
| 3,773,930 | 11/1973 | Mohammed et al. ............ 424/180 |
| 3,920,838 | 11/1975 | Flatt et al. ................. 424/319 |
| 3,950,529 | 4/1976 | Fischer et al. ............... 424/273 |
| 3,964,970 | 6/1976 | Dinelli et al. ............... 195/2 |
| 4,025,650 | 5/1977 | Gans et al. .................. 424/319 |
| 4,053,589 | 10/1977 | Gans et al. .................. 424/177 |
| 4,082,613 | 4/1978 | Thirumalachar et al. ........ 195/76 |
| 4,098,910 | 7/1978 | Evers et al. ................. 426/535 |
| 4,100,160 | 7/1978 | Walser . |
| 4,100,161 | 7/1978 | Walser . |
| 4,100,293 | 7/1978 | Walser . |
| 4,124,448 | 11/1978 | Narasimhan et al. . |
| 4,202,876 | 5/1980 | Monks et al. . |
| 4,216,065 | 8/1980 | Rechnitz et al. . |
| 4,252,822 | 2/1981 | Berry . |
| 4,254,103 | 3/1981 | Timar . |
| 4,259,353 | 3/1981 | Kleinberger . |
| 4,279,917 | 7/1981 | Takami et al. . |
| 4,284,647 | 8/1981 | Brusilow et al. . |
| 4,288,542 | 9/1981 | Johnson et al. . |
| 4,288,546 | 9/1981 | Narasimhan et al. . |
| 4,320,146 | 3/1982 | Walser . |
| 4,352,814 | 10/1982 | Walser . |
| 4,391,909 | 7/1983 | Lim . |
| 4,499,076 | 2/1985 | Ohashi et al. . |
| 4,507,279 | 3/1985 | Okuyama . |
| 4,529,543 | 7/1985 | Renoux et al. . |
| 4,537,852 | 8/1985 | Sugimoto . |
| 4,571,382 | 2/1986 | Adachi . |
| 4,612,302 | 9/1986 | Szabo et al. . |
| 4,687,782 | 8/1987 | Brantman . |
| 4,703,062 | 10/1987 | Blackburn et al. ............ 514/552 |
| 4,704,394 | 11/1987 | Gebo . |
| 4,780,309 | 10/1988 | Geria et al. . |
| 4,792,549 | 12/1988 | Takahashi et al. . |
| 4,849,349 | 7/1989 | Ragg . |
| 4,863,898 | 9/1989 | Ashmead et al. . |
| 4,898,879 | 2/1990 | Madsen et al. . |
| 4,920,098 | 4/1990 | Cotter et al. ................ 514/2 |
| 5,053,387 | 10/1991 | Alexander ................... 514/2 |
| 5,221,668 | 6/1993 | Henningfield et al. .......... 514/23 |
| 5,290,571 | 3/1994 | Bounous et al. .............. 424/535 |

OTHER PUBLICATIONS

Bach et al, *Medium-chain triglycerides: an update*, The American Journal of Clinical Nutrition, vol. 36, pp. 950–962 (1982).

Badley et al, *Diminished Micellar Phase Lipid in Phase Lipid in Patients With Chronic Nonalcoholic Liver Disease and Steatorrhea*, Gastroenterology, vol. 58, No. 6, pp. 781–789 (1970).

Berkowitz et al, *Glucose Tolerance, Free Fatty Acid, and Serum Insulin Responses in Patients with Cirrhosis*, The American Journal of Digestive Diseases, vol. 14, No. 10, pp. 691–699 (1969).

Blendis et al, *Nutrition and Diet in Management of Diseases of the Gastrointestinal Tract*, Modern Nutrition in Health and Disease, Chapter 56, pp. 1182–1200 (1988).

Borum, *Role of Carnitine in Lipid Metabolism*, Lipids in Modern Nutrition, pp. 51–58 (1987).

Bunout et al, *Nutritional Support in Hospitalized Patients With Alcoholic Liver Disease*, European Journal of Clinical Nutrition, vol. 43, pp. 615–621 (1989).

Cabre et al, *Effect of Total Enteral Nutrition on the Short-Term Outcome of Severely Malnourished Cirrhotics*, Gastroenterology, vol. 98, pp. 715–720 (1990).

Charlton et al, *Intensive enteral feeding in advanced cirrhosis: reversal of malnutrition without precipitation of hepatic encephalopathy*, Archives of Diseases in Childhood, vol. 67, pp. 603–607 (1992).

Chawla et al, *Choline May Be an Essential Nutrient in Malnourished Patients With Cirrhosis*, Gastroenterology, vol. 97, pp. 1514–1520 (1989).

Chin et al, *Pre-operative nutritional support in children with end-stage liver disease accepted for liver transplantation: An approach to management*, Journal of Gastroenterology and Hepatology, vol. 5, pp. 566–572 (1990).

DeMoura et al, *Carbohydrate Metabolism Studies in Cirrhosis of the Liver*, American Journal of Digestive Diseases, vol. 13, No. 10, pp. 891–906 (1968).

Egberts et al, *Branched Chain Amino Acids in the Treatment of Latent Portosystemic Encephalopathy*, Gastroenterology, vol. 88, pp. 887–895 (1985).

(List continued on next page.)

*Primary Examiner*—Chhaya D. Sayala
*Attorney, Agent, or Firm*—Hill, Steadman & Simpson

[57] ABSTRACT

A composition is provided that provides a nutritionally complete, calorically-dense formulation suitable for use as a supplement or total enteral feeding. The composition is specifically tailored to meet the requirements of hepatic patients in need of nutritional support. In contrast to current hepatic formulas, the composition is ready-to-use and does not require reconstitution and admixing. The ready-to-use formula contains a protein source that contains at least 25% of its total protein content as free crystalline amino acids.

25 Claims, No Drawings

OTHER PUBLICATIONS

Elias et al, *Association of Spinocerebellar Disorders With Cystic Fibrosis of Chronic Childhood Cholestasis and Very Low Serum Vitamin E,* The Lancet, vol. 2, pp. 1319–1321 (1981).

Garrison et al, *Clarification of Risk Factors for Abdominal Operations in Patients with Hepatic Cirrhosis,* Ann. Surg., vol. 199, No. 6, pp. 648–655 (1984).

Goransson et al, *Low Plasma Tocopherol Levels in Patients With Gastrointestinal Disorders,* Gastroenterology, vol. 8, pp. 21–25 (1973).

Greenberger et al, *Effect of Vegetable and Animal Protein Diets in Chronic Hepatic Encephalopathy,* Digestive Diseases, vol. 22, No. 10, pp. 845–855 (1977).

Guggenheim et al, *Progressive Neuromuscular Disease in Children with Chronic Cholestasis and Vitamin E Deficiency: Clinical and Muscle Biopsy Findings and Treatment With α–Tocopherol,* Annals New York Academy of Sciences, vol. 393, pp. 84–93 (1982).

Halsted et al, *The effect of alcoholism on the absorption of folic acid ($H^3$–PGA) evaluated by plasma levels and urine excretion,* J. Lab & Clin. Med., vol. 69, pp. 116–131 (1967).

Hayes, *"Vitamin–Like" Molecules,* Modern Nutrition in Health and Disease, Chapter 24, pp. 464–470 (1988).

Hepner et al, *Abnormal Vitamin D Metabolism in Patients with Cirrhosis,* Digestive Diseases, vol. 21, No. 7, pp. 527–535 (1976).

Herbert et al, *Correlation of Folate Deficiency with Alchoholism and Associated Macrocytosis, Anemia, and Liver Disease,* Annals of Internal Medicine, vol. 58, No. 6, pp. 977–988 (1963).

Jhangiani et al, *Energy expenditure in chronic alcoholics with and without liver disease,* The American Journal of Clinical Nutrition, vol. 44, pp. 323–329 (1986).

Kearns et al, *Accelerated Improvement of Alcoholic Liver Disease With Enteral Nutrition,* Gastroenterology, vol. 102, pp. 200–205 (1992).

Keohane et al, *Relation between osmolality of diet and gastrointestinal side effects in enteral nutrition,* British Medical Journal, vol. 288, pp. 678–680 (1984).

Kondrup et al, *Nutritional therapy in patients with liver cirrhosis,* European Journal of Clinical Nutrition, vol. 46, pp. 239–246 (1992).

Kondrup et al, *Nutritional Assessment and Adequacy of Dietary Intake in Patients With Alcoholic Liver Cirrhosis,* J Hepatol, Abstract No. 138, p. S35 (1990).

Krause, Ed., *Food, Nutrition and Diet Therapy,* W. B. Saunders, Pub., pp. 714–715 (1979).

Lafiti et al, *Nutrition Support for Liver Failure,* Current Strategies in Surgical Nutrition, vol. 71, No. 3, pp. 567–578 (1991).

Lee, *Diseases of the Liver and Biliary Tract,* Nutrition and Metabolism in Patient Care, Chapter 18, pp. 313–341 (1988).

Leevy et al, *Vitamins and Liver Injury,* The American Journal of Clinical Nutrition, vol. 23, No. 4, pp. 493–499 (1970).

Losowsky et al, *Liver Disease and Malabsorption,* Gastroenterology, vol. 56, No. 3, pp. 589–600 (1969).

Malagelada et al, *Effect of medium–chain triglycerides on liver fatty acid composition in alcoholics with or without cirrhosis,* The American Journal of Clinical Nutrition, vol. 26, pp. 738–743 (1973).

Malagelada et al, *Impaired Absorption of Micellar Long–Chain Fatty Acid in Patients with Alcoholic Cirrhosis,* Digestive Diseases, vol. 19, No. 11, pp. 1016–1020 (1974).

Marchesini et al, *Anticatabolic Effect of Branched–Chain Amino Acid–Enriched Solutions in Patients with Liver Cirrhosis,* Hepatology, vol. 2, No. 4, pp. 420–425 (1982).

McCullough et al, *Nutritional Therapy and liver Disease,* Gastroenterology Clinics of North America, vol. 18, No. 3, pp. 619–643 (1989).

Mezey, *Nutritional state in liver disease, Assessment, incidence and mechanisms of malnutrition,* Metabolism and Nutrition in Liver Disease, pp. 5–15 (1984).

Morgan, *Branched chain amino acids in the management of chronic liver disease,* Journal of Hepatology, vol. 11, pp. 133–141 (1990).

Morgan et al, *Plasma amino–acid patterns in liver disease,* Gut, vol. 23, pp. 362–370 (1982).

Morgan et al, *Nutrition in cryptogenic cirrhosis and chronic aggressive hepatitis,* Gut, vol. 17, pp. 113–118 (1976).

Muñoz, *Nutritional Therapies in Liver Disease,* Seminars in Liver Disease, vol. 11, No. 4, pp. 278–291 (1991).

Nasrallah et al, *Aminoacid Therapy of Alcoholic Hepatitis,* The Lancet, vol. 2, pp. 1276–1277 (1980).

O'Keefe et al, *Malnutrition and Immuno–Incompetence in Patients with Liver Disease,* The Lancet, vol. 2, pp. 615–617 (1980).

Okuno et al, *Postoperative Total Parenteral Nutrition in Patients with Liver Disorders,* Journal of Surgical Research, vol. 39, pp. 93–102 (1985).

Owen et al, *Nature and Quantity of Fuels Consumed in Patients with Alcoholic Cirrhosis,* J. Clin. Invest., vol. 72, pp. 1821–1832 (1983).

Rehfeld et al, *Carbohydrate Metabolism in Alcohol–Induced Fatty Liver,* Gastroenterology, vol. 64, pp. 445–451 (1973).

Romiti et al, *Malabsorption and nutritional abnormalities in patients with liver cirrhosis,* Ital J Gastroenterol, vol. 22, pp. 118–123 (1990).

Rossi–Fanelli et al, *Branched–Chain Amino Acids vs. Lactulose in the Treatment of Hepatic Coma, A Controlled Study,* Digestive Diseases and Sciences, vol. 27, No. 10, pp. 929–935 (1982).

Rudman et al, *Deficiency of Carnitine in Cachectic Cirrhotic Patients,* The Journal of Clinical Investigation, vol. 60, pp. 716–723 (1977).

Shanbhogue et al, *Resting Energy Expenditure in Patients with End–Stage Liver Disease and in Normal Population,* Journal of Parenteral and Enteral Nutrition, vol. 11, No. 3, pp. 305–308 (1987).

Shaw et al, *Influence of Selected Patients Variables and Operative Blood Loss on Six–Month Survival Following Liver Transplantation,* Seminars in Liver Disease, vol. 5, No. 4, pp. 385–393 (1985).

Shepherd et al, *Malnutrition in children with chronic liver disease accepted for liver transplantation: Clinical profile and effect on outcome,* J. Paediatr. Child Health, vol. 27, pp. 295–299 (1991).

Simon et al, *Serum Cholesterol Esterification in Human Liver Disease: Role of Lecithin–Cholesterol Acyltransferase and Cholesterol Ester Hydrolase,* Gastroenterology, vol. 66, No. 4, pp. 539–547 (1974).

Sokol et al, *Mechanism Causing Vitamin E Deficiency During Chronic Childhood Cholestasis,* Gastroenterology, vol. 85, pp. 1172–1182 (1983).

Swart et al, *Elevated protein requirements in cirrhosis of the liver investigated by whole body protein turnover studies,* Clinical Science, vol. 75, pp. 101–107 (1988).

Swart et al, *Minimum Protein Requirements in Advanced Liver Disease, A Metabolic Ward Study of the Effects of Oral Branched Chain Amino Acids,* Metabolism and Clinical Implications of Branched Chain Amino Acids and Ketoacids, pp. 427–432 (1981).

Tasman–Jones et al, *Zinc and Copper Deficiency, With Particular Rerefence to Parenteral Nutrition,* Surg Ann, vol. 10, pp. 23–52 (1978).

Teng et al, *Down–Regulation of Insulin Receptors in Post-necrotic Cirrhosis of the Liver,* Journal of Clinical Endocrinology and Metabolism, vol. 55, No. 3, pp. 524–530 (1982).

Teichberg et al, *Response of Rat Intestine to a Hyperosmotic Feeding,* Pediatr Res, vol. 12, pp. 720–725 (1978).

Vlahcevic et al, *Bile Acid Metabolism in Patients With Cirrhosis,* Gastroenterology, vol. 60, No. 4, pp. 491–498 (1971).

Watanabe et al, *Effect of a Branched Chain Amino Acid–Enriched Nutritional Product on the Pathophysiology of the Liver and Nutritional State of Patients with Liver Cirrhosis,* Acta Med. Okayama, vol. 37, No. 4, pp. 321–333 (1983).

Silk et al., Gut Supplement, pp. 529–533, 1991.

Jacqueline Barber et al., Clinical Pharmacy, vol. 3, pp. 245–253, 1984.

O'Keefe et al J. Parent. Ent. Nutr., vol. 11(5) pp. 447–453, (1987).

Shronts et al J. Am. Diet. Assoc. vol. 87(4) pp. 441–448 (1987).

COMPOSITION AND METHOD FOR TREATING PATIENTS WITH HEPATIC DISEASE

BACKGROUND OF THE INVENTION

The present invention relates generally to methods and compositions for treating patients who have hepatic disease. More specifically, the present invention relates to an enteral composition specifically designed for patients with hepatic disease.

The liver, and its proper functioning, is of utmost importance to the survival of a patient. Because it is responsible for the metabolism of nearly all nutrients, and is the primary site for the inactivation of numerous toxins, the liver is one of the most important organs of the body. For example, the liver accounts for approximately 20% of the body's basal metabolism.

The liver extracts a majority of the amino acids, carbohydrates, lipids, vitamins, and minerals from portal circulation. These nutrients, extracted by the liver, are used as substrates or cofactors in all metabolic processes carried out in the liver. Synthesis of plasma proteins and bile secretion are additionally important processes carried out by the liver.

Due to a variety of insults and pathogens, the liver can become diseased. Liver disease is a broad classification encompassing a number of acute and chronic diseases. These diseases include: hepatitis (viral and non-viral); cirrhosis (alcoholic and non-alcoholic); and liver failure. Liver failure is perhaps the most severe disease and may be accompanied by a complex set of conditions including: hepatic encephalopathy; hemorrhage; coagulapathy; ascites; jaundice; and hepatorenal syndrome.

Although many medical treatments have been devised for treating liver disease, due to the paradoxical relationship between hepatic function and metabolism, medical treatment of the liver disease is complex and difficult. Most, if not all, liver diseases require or benefit from nutritional management. Those diseases which are believed to benefit most from nutritional management, include alcoholic and non-alcoholic cirrhosis, obstructive jaundice, and in some situations acute liver failure. The goals of such nutritional therapies vary depending on disease and patient. The goals can be either restorative or supportive.

Liver disease can affect both hepatic cellular function and structure. In chronic conditions such as alcoholic cirrhosis, exposure to a toxicant promotes inflammation of the periportal areas of the liver. As a result, fibrosis develops and when sufficiently advanced, canaliculi become blocked. As a result of inadequate regional perfusion, hepatocyte degeneration occurs.

In an attempt to restore adequate circulation, portal hypertension develops. Portosystemic shunting of the blood results in chronic hypertension. Many of the serious complications of liver disease are due to this event.

Portosystemic shunting allows many substances, for example, amino acids, fatty acids, ammonia, and others, to bypass the liver. These substances then flood the neurological system. Portosystemic shunting results in many clinical features including variceal changes and encephalopathy.

Many specific metabolic derangements are associated with liver disease. This is especially true of liver disease of a chronic nature. Such derangements include: increased plasma glucagon; hyperinsulinemia; increased plasma epinephrine and cortisol; decreased liver and muscle carbohydrate stores; accelerated gluconeogenesis; hypoglycemia; hyperammonemia; increased plasma aromatic amino acid; increased plasma methionine, glutamine, asparagine, and histidine; and decreased plasma branched chain amino acids.

A number of hypotheses, mostly metabolism based, have been advanced concerning the pathogenesis of hepatic encephalopathy. For example, excess nitrogen (ammonium) production and accumulation of false neural transmitters have been advanced as possible causes.

Although a number of nutritional formulations designed for hepatic patients had been proposed none of the formulations, in the opinion of the inventors, function entirely satisfactorily. Such formulations include: Amin-Aid® (Kendall-McGaw); and Travasorb® Hepatic (Clintec Nutrition Company).

One disadvantage with these formulations is that they are not ready to use. Rather, they are powders that require admixing and reconstitution before use. Powders that require admixing create disadvantages including sterility, labor, and time concerns.

Although a ready-to-use formulation would be desirable and greatly preferred over a powder, there are difficulties in attempting to create a ready-to-use formulations. The difficulties have, to the best of the inventors' belief, prevented the creation of viable ready-to-use hepatic enteral formulations. The difficulties include the instability of solutions containing free crystalline amino acids.

There is therefore a need for an improved nutritional formulation for patients with liver disease.

SUMMARY OF THE INVENTION

The present invention provides in part, a ready-to-use enteral composition specifically designed for patients with liver disease. The composition is a nutritionally complete, calorically-dense formulation suitable for use as a supplement or total enteral feeding. The composition is specifically tailored to meet the requirements of hepatic patients in need of nutritional support. In contrast to current hepatic formulas, the composition is ready-to-use and does not require reconstitution and admixing.

To this end, the present invention provides a ready-to-use formula containing a protein source that contains at least 25% of its total protein content as free crystalline amino acids. Preferably, a majority of the protein source is present as free crystalline amino acids, i.e., greater than 50%. In an embodiment, approximately 75% of the protein is provided as free crystalline amino acids.

In an embodiment, the composition contains approximately 6% to about 16% of the calories as protein; approximately 66% to about 88% of the calories as carbohydrate; and approximately 6% to about 18% as lipid. Additionally, the composition preferably meets or exceeds 100% of the U.S. RDA for vitamins and minerals in 1000 ml (1500 K cal) of product.

Preferably protein is provided in the form of a combination of free crystalline amino acids and high quality whey protein. Preferably the amino acid profiles are rich in branched amino acids (approximately 40% to about 60% of the total amino acid content) and is low in aromatic and ammonia-generating amino acids (less than preferably 3% of the total amino acid content).

In an embodiment, the carbohydrate is supplied in the form of easily-digestible maltodextrin and starch.

In an embodiment lipid is supplied as a mixture of medium chain triglycerides (approximately 50% to about 75% of the lipid source), canola oil, corn oil, and soy lecithin. The lipid source also provides a balanced supply of essential fatty acids in a readily absorbable, oxidizable lipid source.

In an embodiment, the lipid has a ratio of omega-6 to omega-3 fatty acids of approximately 4:1.

Preferably, the composition is gluten free and low in sodium.

A method of treating hepatic patients is also provided by the present invention as well as a method for making nutritional formulations for hepatic patients.

Still further, an advantage of the present invention is to provide a composition that provides improved utilization and metabolism of both the omega-6 and omega-3 families.

An advantage of the present invention is that it provides a ready-to-use enteral diet specifically designed for patients with liver disease.

A further advantage of the present invention is that the composition of the present invention is specifically tailored to meet the requirements of hepatic diseased patients.

Additionally, an advantage of the present invention is to provide a stable, ready-to-use formula, including a protein composition that comprises greater than 50% of its content as free crystalline amino acids.

Still further, an advantage of the present invention is that the composition of the present invention provides a protein content that is designed to meet nutritional requirements, promote muscle anabolism and minimize ammonium production, but limit intake in persons who are protein intolerant.

Furthermore, an advantage of the present invention is that it provides a composition including carbohydrates which are easily digestible and well absorbed.

Another advantage of the present invention is that in an embodiment, the composition is lactose-free thus eliminating the risk of developing symptoms of lactose intolerance.

Moreover, an advantage of the present invention is that the composition provides, in part, medium chain triglyceride that are well absorbed and a readily oxidizable sources of calories.

Still further, an advantage of the present invention is that the composition provides at least 100% of the U.S. RDA of vitamins and minerals.

Furthermore, an advantage of the present invention is that the composition meets the stress augmented needs of most patients.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides an enteral composition specifically designed for patients with hepatic disease. The composition is nutritionally complete, calorically dense, and suitable as a supplement or a total enteral feeding—either by tube or orally. The composition is specifically tailored to meet the requirements of hepatic patients in need of nutritional support.

In contrast to current hepatic formulations, the composition is ready-to-use. Because the product is shelf stable, it is not provided to the patient or healthcare practitioner as a powder. Therefore, the composition does not require reconstitution by the patient or healthcare practitioner. Although the composition is ready-to-use, it still provides sufficient free crystalline amino acids to function as a nutritionally complete hepatic composition.

In an embodiment, the composition contains: approximately 6% to 16% of the calories as a protein source; approximately 66% to about 88% of the calories as a carbohydrate source; and approximately 6% to about 18% of the calories as a lipid source. In a preferred embodiment, the composition comprises approximately 11% of the calories as protein; approximately 77% of the calories as carbohydrate; and approximately 12% as lipid. The composition is specifically tailored to meet the needs of liver diseased patients. As set forth in the background of the invention, these patients suffer the possibility of a number of derangements.

Because of the liver's fundamental role in the metabolism of nearly all nutrients, hepatic disease can easily compromise nutritional status. Therefore, malnutrition is common in hepatic diseased patients. It has been estimated, with respect to alcoholic cirrhotics with severe liver disease, that 10% to 100% of such patients are malnourished. See, McCulloush et al, *Nutritional State in Liver Disease Assessment, Incidence and Mechanism of Malnutrition*, Metabolism and Nutrition in Liver Disease, E. Holm et al (Editors) 1984, p. 5–15. This malnutrition develops as a result of a number of factors including: anorexia; nutrient malabsorption and maldigestion; reduced food intake; and possibly increased energy expenditure.

Malabsorption also frequently occurs in patients with liver disease particularly in malnourished patients. Fat malabsorption is frequent; in one study, 8 out of 13 malnourished cirrhotics demonstrated fat malabsorption. Romiti et al, *Malabsorption and Nutritional Abnormalities in Patients with Liver Disease*, Ital. J. Gastroenterol., 1990; 22:118–123.

It is necessary for the hepatic composition of the present invention to provide adequate energy intake to support protein synthesis. If energy intakes are inadequate, amino acids will be used to support energy demands. Conversely, excess caloric intake will result in increased deposition of fat in the liver; this can result in further metabolic impairment of the liver. The composition of the present invention provides normal nutritional status and supports hepatocyte regeneration.

Although most stable cirrhotic patients have no overt problems digesting and absorbing protein and amino acids, investigators have reported derangements in such patient's plasma amino acid profiles. See, Morgan et al, *Plasma Amino Acid Patterns In Liver Disease*, Gut 1982; 23:362–370. This suggests altered tissue utilization of amino acids. For example, plasma levels of leucine, isoleucine, and valine concentrations in hepatic patients are low. Additionally, methionine and aromatic amino acids, i.e., tryptophan, tyrosine, and phenylalanine, concentrations are elevated. The composition of the present invention is specifically tailored to correct these abnormalities.

The composition of the present invention provides 6% to 16% of the composition, by caloric content, as protein. In a preferred embodiment 11% of the composition, by caloric content, is provided as protein or 40 g of protein per liter (1500 kcals). Pursuant to the present invention, the protein comprises at least 25% and preferably 50% free crystalline amino acids. In a preferred embodiment, almost 75% of the protein is free crystalline amino acids. It has been found that by providing approximately 20%–40%, preferably 20%–25%, of the protein as whey or other protein, a free amino acid rich protein source that is sufficiently stable can be provided.

The protein is preferably provided as a mixture of specific essential and non-essential amino acids and whey protein. The amino acid profile is rich in branched chain amino acids, preferably approximately 40% to about 60%, and most preferably 50%, and low in ammonotelic amino acids (3%) in order to offset the amino acid derangements associated with hepatic disease. The total protein content is designed to meet the nutritional requirements, promote muscle anabolism, and minimize ammonia production, but limit intake in persons who are protein intolerant.

The use of enriched branched amino acids is advantageous especially with respect to treating hepatic encephalopathy. It is believed that branched chain amino acids can either improve recovery from or, in combination with other therapy, improve such treatment. Additionally, branched chain amino acids can decrease protein catabolism, increase synthesis of hepatic and muscle protein, and serve as energy substrates for muscle tissues. Ammonia production may also be reduced when branched chain amino acids are given as a substrate. Further, branched chain amino acids can improve nitrogen balance.

During bouts of encephalopathy, protein restrictions below that required to maintain body stores, is often prescribed (less than 0.8 grams protein per Kg per day). This, however, often results in negative nitrogen balance and additional loss of the lean body mass, ultimately contributing to further decline in nutritional and perhaps disease status. Accordingly, pursuant to the present invention, protein intake is carefully matched to the requirements to achieve optimal repletion with minimum negative clinical consequences. The amino acid profiles are customized to meet protein requirements and correct disease related changes in amino acid metabolism.

One of the principal metabolic defects in patients with liver disease is glucose intolerance. Elevations in glucagon, free fatty acids, and growth hormone are commonly observed in such patients and may serve to sustain high insulin levels and exacerbate glucose intolerance.

The composition of the present invention provides 66% to about 88% of the caloric content as carbohydrates. In a preferred embodiment, the composition provides 77% of the calories, or 290 grams of carbohydrates per liter (1500 kcals) are provided. In a preferred embodiment, the carbohydrates are provided in the form of maltodextrin and modified corn starch. These are easily digested and well absorbed.

Additionally, preferably, the composition is virtually lactose free. This eliminates the risk of the hepatic patients developing symptoms of lactose intolerance.

With respect to the lipid content, primary metabolic derangement of lipid metabolism in liver disease patient is lipid malabsorption. The cause of fat malabsorption may vary depending on the nature and severity of the liver disease. Non-alcoholic cirrhotics manifest normal gut histology while alcoholic cirrhotics show some evidence of jejunal damage. In both populations there is likely to be a reduction in bile salt synthesis, which also contributes to fat malabsorption.

In an embodiment, the composition of the present invention provides approximately 6% to about 18% of the calories as lipid. However, the composition could provide up to 25% of the calories as lipid. In a preferred embodiment, the composition provides 12% of the caloric content, or 21 g lipid per liter (1500 kcals), in the form of lipids. In a preferred embodiment, the lipid content comprises a blend of medium chain triglyceride oil and long chain fatty acids.

Preferably, the blend of medium chain triglycerides to long chain triglycerides is 1:1 to about 3:1. In a preferred embodiment, a 66:34% blend of medium chain triglyceride oil and long chain fatty acids is provided. Medium chain triglycerides are well absorbed and a readily oxidizable source of calories. The substitution of medium chain triglycerides for long chain fatty acids, the inventors believe, will alleviate steatorrhea in some patients. In a number of hepatic patients—believed to be at least 10%—steatorrhea is severe.

To provide essential fatty acids, in an embodiment, canola oil, milk fat, corn oil, and/or soy lecithin are provided. Linoleic and linolenic acid are provided preferably in a proportion of 3:1 to 5:1 and, most preferably, 4:1.

Hepatic patients have, typically, abnormalities of vitamin nutriture. However, assessment of vitamin and mineral status of hepatic patients is very difficult. Commonly used plasma measurements may be profoundly altered by portosystemic shunting and hepatocyte degeneration. Depressed synthesis of visceral proteins may also influence plasma concentrations of vitamins, therefore, it is difficult to accurately characterize in a hepatic patient the severity of vitamin and mineral deficiencies.

However, it is clear that in hepatic patients, widespread suboptimal vitamin nurture is common. In general, hepatic stores of riboflavin, nicotinamide, pantothenic acid, and Vitamins B6, B12, and A are often depleted. See, Leevy et al, *Vitamin and Liver Injury*, Am. J. Clin. Nutr. 1970; 23: 493–499. The absorption of all fat soluble vitamins is also adversely affected by hepatic diseased.

Vitamin A status is often impaired in liver disease with severity and type of the disease being significant determinants of its gravity. Fat malabsorption secondary to bile acid deficiency, may also contribute to the development of vitamin A deficiency.

Normally, Vitamin D3 is transported to hepatic tissue. In the liver, Vitamin D3 is converted to 25-hydroxy Vitamin D3. The active form of the vitamin (1, 25 dihydroxy Vitamin D3) is due to a hydroxylation step that occurs in the kidney. Liver disease impairs the export of 25 hydroxy Vitamin D3 from the liver. See, Hepner G. et al, *Abnormal Vitamin D Metabolism in Patients With Cirrhosis*, Am. J. Dig. Dis., 1976; 21:527–535. Even though hepatic patients have normal serum levels of Vitamin D, they may therefore have reduced tissue stores.

Likewise, vitamin E status may be compromised by hepatic disease. This is particularly true with patients with malabsorption and diminished bile secretion. Vitamin K status may also be compromised. This may be attributed to both malabsorption and cholestasis.

Water soluble vitamin nutriture may be similarly deranged particularly in the case of pyridoxine, thiamine, folate, riboflavin, and vitamin B12. Folate deficiency is the most common aberration in hepatic disease patients, especially alcoholic cirrhotics. Clinically, anemia can develop in 3 to 6 weeks as a result of subnormal folate intake.

Deficiency of vitamin B12 can also develop in chronic liver disease.

Mineral nutriture may also be abnormal in patients with liver disease. Liver enzymes require as cofactors a number of trace elements, i.e. zinc, copper, nickel, selenium, chromium, and cobalt. Cirrhosis can readily deplete liver stores of these minerals, particularly zinc and copper. Deficiencies or depletion may contribute to poor tissue repair and possibly neurological abnormalities.

Hyponatremia is relatively common in cirrhotic patients. This state develops in conjunction with an increase in the total body sodium pool which results in fluid retention. Increased sodium retention appears to result from increase aldosterone production. It is necessary to restrict sodium intake to reduce ascites and edema.

Hypokalemia occurs frequently among cirrhotic patients. If not managed properly, hypokalemic alkalosis develops and hepatic encephalopathy may develop or worsen. Therefore, control of dietary intake of potassium relative to other minerals is vital.

Due to hepatic disease, calcium, phosphorus, and magnesium stores are also depleted. This depletion can be linked to a number of derangements, e.g., metabolic bone disease.

The present invention provides preferably in 1500 kcal (1000 mls) at least 100% U.S. RDA of all vitamins except vitamin C. Vitamin C is provided at at least 150% of the U.S. RDA to meet stress augmented needs in most patients.

Additionally the composition provides 100% of U.S. RDA of calcium, phosphorus, magnesium, copper, iodine, iron, and zinc in 1500 kcals (1000 millimeters). In a preferred embodiment manganese is provided in concentrations of approximately 4 milligrams per 1500 kcals. Additionally, the composition also provides preferably approximately 400 mg Choline per 1500 kcals.

Additionally, approximately 80 milligrams sodium, 330 milligrams potassium, and 375 milligrams chloride are provided per 250 ml. These concentrations allow flexibility in electrolyte management.

Little is known about the specific taurine and carnitine status or requirements for patients with liver disease. Taurine stores have been found to be depressed in patients with malabsorption syndromes. Additionally, liver malfunction is known to impair taurine synthesis. Biosynthesis of carnitine may also be reduced when liver function is abnormal. Preferably, the composition of the present invention provides approximately 120 mg taurine and 120 mg carnitine per 1500 kcals.

By way of example, and not limitation, an example of the composition of the present will now be given.

COMPOSITION:

|  |  | 1000 ml |
|---|---|---|
| Protein (Nx 5.8) | g | 40.00 |
| Carbohydrate | g | 290.00 |
| Fat | g | 21.20 |
| Minerals | g | 8.00 |
| Moisture | g | 761.60 |
| Energy | Kcal | 1500.00 |
|  | KJ | 6280.00 |
| Vitamin A | IU | 5000.00 |
|  | mcg RE | 1500.00 |
| Vitamin D | IU | 400.00 |
|  | mcg | 10.00 |
| Vitamin E | IU | 30.00 |
| Vitamin K | mcg | 120.00 |
| Vitamin C | mg | 96.00 |
| Thiamine (B1) | mg | 1.52 |
| Riboflavin (B2) | mg | 1.72 |
| Niacin (PP) | mg | 20.00 |
| Vitamin B6 | mg | 2.00 |
| Folic Acid | mcg | 400.00 |
| Pantoth. Acid | mg | 10.00 |
| Vitamin B12 | mcg | 6.00 |
| Biotin | mcg | 300.00 |
| Choline | mg | 400.00 |
| Taurine | mg | 120.00 |
| L-Carnitine | mg | 120.00 |

-continued

| Sodium | mg | 320.00 |
|---|---|---|
| Potassium | mg | 1320.00 |
| Chloride | mg | 1500.00 |
| Calcium | mg | 1000.00 |
| Phosphorus | mg | 1000.00 |
| Magnesium | mg | 400.00 |
| Copper | mg | 2.00 |
| Iodine | mcg | 152.00 |
| Iron | mg | 18.00 |
| Manganese | mg | 4.00 |
| Zinc | mg | 15.20 |

Density = 1125 g/Liter
pH 6.8

FAT COMPOSITION:

|  |  | 1000 ml |
|---|---|---|
| Total fat | g | 21.2 |
| MCT | g | 13.76 |
| Canola Oil | g | 4.16 |
| Corn Oil | g | 1.12 |
| Milk Fat | g | 1.12 |
| Lecithin | g | 1.12 |
| Linoleic Acid | g | 1.58 |
| Vitamin E | IU | 30 |

Vitamin E: linoleic = 19 IU/gm

PERCENTAGE COMPOSITION OF FAT:

| MCT | 66% | (63% of energy from fat) |
|---|---|---|
| Canola oil | 19% | (20% of energy from fat) |
| Corn oil | 5% | (5.5% of energy from fat) |
| Milk Fat | 5% | (5.5% of energy from fat) |
| Lecithin | 5% | (6% of energy from fat) |
| Total | 100% | Total 100% |

FATTY ACID COMPOSITION (CALCULATED FROM STANDARD VALUES):

|  |  | Calculated from standard values | |
|---|---|---|---|
| Fatty acid composition |  | (% of total fatty acids) | (g/liter) |
| Saturated | | | |
| Butyric acid | ($C_4$:0) | 0.13 | 0.03 |
| Caproic acid | ($C_6$:0) | 0.72 | 0.14 |
| Caprylic acid | ($C_8$:0) | 38.36 | 7.42 |
| Capric acid | ($C_{10}$:0) | 27.02 | 5.23 |
| Lauric acid | ($C_{12}$:0) | 1.43 | 0.28 |
| Myristic acid | ($C_{14}$:0) | 0.47 | 0.09 |
| Palmitic acid | ($C_{16}$:0) | 2.80 | 0.54 |
| Stearic acid | ($C_{18}$:0) | 1.16 | 0.22 |
| Total saturated | | 72.09 | 13.95 |
| Unsaturated | | | |
| Palmitoleic acid | ($C_{16}$:1) | 0.25 | 0.05 |
| Oleic acid | ($C_{18}$:1) | 16.74 | 3.24 |
| Liolenic acid | ($C_{18}$:2) | 8.38 | 1.62 |
| Linolenic acid | ($C_{18}$:3) | 2.16 | 0.42 |
| Erucic acid | ($C_{22}$:1) | 0.40 | 0.08 |
| Total unsaturated | | 27.93 | 5.41 |

PROTEIN COMPOSITION:

| Protein Source: | Free Amino Acid | 77% |
|---|---|---|
|  | Whey | 23% |
| Nitrogen to energy ratio (g N/kcal): | | 1:217 |
| Nitrogen to non-protein energy ratio (g N/kcal): | | 1:194 |

AMINO ACID COMPOSITION:

|  |  | 100 Kcal | 1500 Kcal | 250 ml | 1000 ml |
|---|---|---|---|---|---|
| L-Leucine | gm | 0.62 | 9.32 | 2.33 | 9.32 |
| L-Isoleucine | gm | 0.51 | 7.72 | 1.93 | 7.72 |
| L-Valine | gm | 0.41 | 6.20 | 1.55 | 6.20 |
| L-Lysine | gm | 0.33 | 5.00 | 1.25 | 5.00 |
| L-Arginine | gm | 0.32 | 4.80 | 1.20 | 4.80 |
| L-Proline | gm | 0.17 | 2.48 | 0.62 | 2.48 |
| L-Glutamic acid | gm | 0.14 | 2.08 | 0.52 | 2.08 |
| L-Alanine | gm | 0.13 | 1.88 | 0.47 | 1.88 |
| L-Threonine | gm | 0.10 | 1.52 | 0.38 | 1.52 |
| L-Histidine | gm | 0.10 | 1.44 | 0.36 | 1.44 |
| L-Aspartic acid | gm | 0.07 | 1.04 | 0.26 | 1.04 |
| Glycine | gm | 0.05 | 0.76 | 0.19 | 0.76 |
| L-Serine | gm | 0.04 | 0.64 | 0.16 | 0.64 |
| L-Methionine | gm | 0.04 | 0.56 | 0.14 | 0.56 |
| L-Phenylalanine | gm | 0.03 | 0.40 | 0.10 | 0.40 |
| L-Tyrosine | gm | 0.02 | 0.32 | 0.08 | 0.32 |
| L-Tryptophane | gm | 0.02 | 0.24 | 0.06 | 0.24 |
| L-Cystine | gm | 0.01 | 0.16 | 0.04 | 0.16 |

MAJOR MINERALS

|  |  | 100 Kcal | 1500 Kcal | 250 ml | 1000 ml |
|---|---|---|---|---|---|
| Sodium | mg | 21.33 | 320.00 | 80.00 | 320.00 |
|  | mmol | 0.93 | 13.92 | 3.48 | 13.92 |
| Potassium | mg | 88.00 | 1320.00 | 330.00 | 1320.00 |
|  | mmol | 2.25 | 33.76 | 8.44 | 33.76 |
| Chloride | mg | 100.00 | 1500.00 | 375.00 | 1500.00 |
|  | mmol | 2.82 | 42.32 | 10.58 | 42.32 |
| Calcium | mg | 66.67 | 1000.00 | 250.00 | 1000.00 |
|  | mmol | 1.67 | 25.00 | 6.25 | 25.00 |
| Phosphorus | mg | 66.67 | 1000.00 | 250.00 | 1000.00 |
|  | mmol | 2.15 | 32.24 | 8.06 | 32.24 |
| Magnesium | mg | 26.67 | 400.00 | 100.00 | 400.00 |
|  | mmol | 1.10 | 16.44 | 4.11 | 16.44 |
| Base excess (1) | mmol | 0.36 | 5.36 | 1.34 | 5.36 |
| Renal solute load (2) | mOsm | 21.20 | 318.00 | 29.50 | 318.00 |

ELECTROLYTE RATIOS

Na/K (3):0.4
(Na + K)/Cl (3):1.1
Ca/P (4):1.0

FORMULA OSMOLARITY/OSMOLALITY

| Osmolarity | 525 mOsm/l |
|---|---|
| Osmolarity | 690 mOsm/kg H₂O |

The osmolarity of such liquid diets is important. Because hypertonic diets are a cause of diarrhea and intestinal discomfort in patient on enteral feeding, hyperosmolar formulas initially have to be fed diluted and only gradually be increased to full strength. When a patient is not taking a formula full strength, he meets neither his energy nor his protein, mineral, and vitamin needs. There is also evidence that hypertonic foods have a deleterious effect on the gastrointestinal tract.

The osmolarity of the composition is preferably at least 500 mOsm/l and, in a preferred embodiment, 525 mOsm/l (690 mOsm/kg of water). This is hypertonic with serum (osmolarity 260–280 mOsm/ml, osmolality 280–300 mosmol/kg of water) and should not be expected to cause any problems.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A shelf stable ready-to-use composition for providing nutritional support for a hepatic patient, that does not require reconstitution and can be stored in a liquid form comprising:
   a lipid component;
   a carbohydrate component; and
   a protein component that comprises at least 25% by protein content free amino acids and a storage stabilizing amount of whey protein.

2. (Amended) The composition of claim 1 wherein:
   the protein component comprises approximately 6% to about 16% of the caloric content of the composition;
   the lipid component comprises approximately 6% to about 18% of the caloric content; and
   the carbohydrate component comprises comprise approximately 66% to about 88% of the caloric content of the composition.

3. The composition of claim 1 wherein the free amino acids comprise greater than 50% by weight of the total protein source.

4. A shelf stable ready-to-use liquid composition for providing nutritional support to a patient having hepatic disease, the composition comprising:
   approximately 6% to about 16%, by caloric content of the composition, of a protein component that comprises greater than 50% by weight of its content as free crystalline amino acids, the protein component further including a storage stabilizing amount of whey protein;
   approximately 6% to about 25%, by caloric content of the composition, of a lipid component; and
   approximately 66% to about 88% by caloric content of the composition as a carbohydrate component.

5. The composition of claim 4 wherein the amino acids are comprised of 40% to 60% branched chain amino acids.

6. The composition of claim 4 wherein the amino acids include greater than 0% and less than 3% aromatic and ammonia-generating amino acids.

7. The composition of claim 4 including at least 100% of the U.S. RDA of all vitamins per 1500 Kcals of composition and at least 150% of the U.S. RDA of vitamin C.

8. The composition of claim 4 wherein the lipid component is a mixture of medium chain triglycerides and long chain fatty acids.

9. The composition of claim 8 wherein the ratio of medium chain triglycerides to long chain fatty acids is 1:1 to 3:1.

10. The composition of claim 4 wherein the lipid component has a ratio of omega-6 to omega-3 fatty acids of 4:1.

11. The composition of claim 4 wherein the composition provides 100% of the U.S. RDA for calcium, phosphorus, magnesium, copper, iodine, iron, and zinc per 1500 Kcals of composition.

12. The composition of claim 4 wherein the osmolarity of the composition is at least 500 mOsm/L.

13. The composition of claim 4 wherein the free crystalline amino acids include: leucine; isoleucine; valine; lysine; arginine; proline; glutamic acid; alanine; threonine; histidine; aspartic acid; glycine; serine; methionine; phenylalanine; tyrosine; tryptophane; and cystine.

14. A shelf stable, ready-to-use liquid composition for providing nutritional support to a hepatic patient, the composition comprising:
   (a) from about 6% to about 16% of the protein component, based on the total caloric content of the composition, the protein component including at least about 25% by weight of a free, crystalline amino acid fraction and at least about 20% by weight of a whey protein fraction, based upon the weight of the protein component, the amino acid fraction including at least about 40% of branched chain amino acids and greater than 0% and less than about 3% of aromatic and ammonia-generating amino acids;

(b) from about 66% to about 88% of the carbohydrate component, based on the total caloric content of the composition; and (c) from about 6% to about 18% of a lipid component, based on the total caloric content of the composition, the lipid component including a mixture of medium chain triglycerides and long chain fatty acids and having a ratio of omega-6 to omega-3 fatty acids of about 4:1, the composition being storable in liquid form without requiring reconstitution or dilution prior to use.

15. The composition of claim 14 wherein the whey comprises approximately 25% to about 40% of the protein component.

16. The composition of claim 14 wherein the amino acid fraction comprises 40% to 60% branched chain amino acids.

17. The composition of claim 14 wherein the free crystalline amino acid fraction includes: leucine; isoleucine; valine; lysine; arginine; proline; glutamic acid; alanine; threonine; histidine; aspartic acid; glycine; serine; methionine; phenylalanine; tyrosine; tryptophane; and cystine.

18. The composition of claim 14 including at least 100% of the U.S. RDA of all vitamins per 1500 Kcals of composition and at least 150% of the U.S. RDA of vitamin C.

19. The composition of claim 14 wherein the ratio of medium chain triglycerides to long chain fatty acids is 1:1 to 3:1.

20. The composition of claim 14 wherein the composition provides 100% of the U.S. RDA for calcium, phosphorus, magnesium, copper, iodine, iron, and zinc per 1500 Kcals of composition.

21. A method for preparing a shelf stable liquid ready-to-use nutritional product comprising the steps of:

providing a lipid component;

providing a carbohydrate component;

providing a protein component that includes free crystalline amino acids; and adding to the protein component whey protein in an amount that comprises less than 50% by weight of the protein component but is sufficient to stabilize a solution that comprises the combination of the lipid, carbohydrate, and protein component.

22. A method for providing nutrition to a hepatic patient comprising the steps of:

administering enterally to a patient with liver disease a shelf stable composition that does not require reconstitution that comprises:

approximately 6% to about 16% by caloric content of the composition, of a protein component that comprises more than 50% by weight of its content as free crystalline amino acids;

approximately 6% to about 25%, by caloric content of the composition, of a lipid component; and approximately 66% to about 88%, by caloric content of the composition, as a composition, as a carbohydrate component, the protein component further including a stabilizing amount of whey protein.

23. The method of claim 22 wherein the composition is administered through a naso-gastric feeding tube.

24. The method of claim 22 wherein the composition is administered by having the patient drink the composition.

25. The method of claim 22 wherein the composition provides complete nutritional support for the patient.

* * * * *